United States Patent [19]

Nakajima et al.

[11] 4,362,162
[45] Dec. 7, 1982

[54] SURGICAL SUTURES

[75] Inventors: Takeaki Nakajima, Ibaragi; Tatsushiro Yoshimura, Takatsuki; Yukihiko Karasawa, Tokyo, all of Japan

[73] Assignee: Daikin Kogyo Co., Ltd., Osaka, Japan

[21] Appl. No.: 246,382

[22] Filed: Mar. 23, 1981

[30] Foreign Application Priority Data

Mar. 26, 1980 [JP] Japan ................................ 55-39220

[51] Int. Cl.$^3$ ............................................ A61B 17/00
[52] U.S. Cl. ................................ 128/334 R; 428/372; 428/394; 428/395
[58] Field of Search ............... 128/334; 428/372, 375, 428/378, 394, 395; 526/254

[56] References Cited

U.S. PATENT DOCUMENTS

Re. 27,028  1/1971  Ely, Jr. et al. ...................... 526/254
2,520,173  8/1950  Sanders ............................... 526/254
2,549,935  4/1951  Sauer ................................... 526/254
3,665,927  5/1972  Kurtz ................................... 428/372

Primary Examiner—V. Millin
Assistant Examiner—Nancy A. B. Swisher
Attorney, Agent, or Firm—Armstrong, Nikaido, Marmelstein & Kubovcik

[57] ABSTRACT

A surgical suture which is filled with copolymer of tetrafluoroethylene and another polymerizable monomer and has outstanding properties, and a process for preparing the same.

3 Claims, 2 Drawing Figures

SURGICAL SUTURES

This invention relates to surgical sutures, and more particularly to multifilamentous sutures.

Surgical sutures generally used include monofilamentous sutures and multifilamentous sutures. Although monofilamentous sutures are solid, free from interstices and usually smooth-surfaced and have the drawback of being inferior in knotting characteristics, these sutures have the advantage that they will not readily attach to the tissue of the human body because their surfaces have a low coefficient of friction. Multifilamentous sutures are prepared by twisting or braiding bundles of many long filaments of polyester or the like in a complex manner, therefore have interstices in its interior and a higher coefficient of friction than monofilamentous sutures, and are disadvantageous in that the tissue of the human body is likely to enter the interstices and attached to the suture, whereas they have the advantage of being generally superior in knotting characteristics. In order to assure the advantage of multifilamentous sutures and overcome the drawback thereof, multifilamentous sutures have been developed in which the minute interstices between the fibers are filled with polytetrafluoroethylene (hereinafter referred to as "PTFE") as disclosed, for example, in U.S. Pat. Nos. 3,390,681, 3,379,552 and 3,322,125. Although in actual use even, such improved sutures are not always satisfactory in respect of all the properties mentioned above.

Furthermore, a detailed examination of the improved multifilamentous suture reveals that when the suture is subjected to an external force, especially to a shearing force, numerous fine fibrous whiskers are formed on the surfaces of PTFE particles retained in the interstices. This phenomenon, which is peculiar to PTFE, occurs readily when the twisted or braided material is immersed in a suspension of PTFE for impregnation, dried or otherwise handled to fill the fiber-to-fiber interstices with PTFE and also when the impregnated material is stretched for the production of the suture. Consequently it becomes impossible to fill the interstices with PTFE to the desired extent. Moreover, the fine fibrous whiskers form interstices on the surface of the suture. The presence of the whiskers permits the suture to attach to the human body tissue more readily, while such whiskers will be released into the blood, possibly causing a thrombus.

The main object of this invention is to overcome the foregoing problems heretofore encountered with the sutures filled with PTFE and to provide surgical sutures having outstanding slipping properties.

The above and other objects of the invention as well as features thereof will become apparent from the following description.

To fulfill the objects, the present invention provides a surgical suture characterized in that a multifilamentous suture has incorporated in its interstices a copolymer of tetrafluoroethylene (hereinafter referred to as "TFE") and the other copolymerizable monomer in an amount of about 1 to about 30% by weight based on the weight of the multifilamentous suture, the copolymer being up to 300 m$\mu$ in mean particle size, and that the portion of the copolymer present at least in the vicinity of the surface of the suture has been baked.

The surgical sutures of this invention retain the copolymer particles free of deformation, especially without the formation of fine fibrous whiskers, even when subjected to an external force unlike the conventional PTFE-impregnated sutures, have a lower coefficient of friction and improved knotting characteristics and possess the favorable properties of mono- and multi-filamentous sutures.

As a rule, the TFE copolymer to be used in this invention is a copolymer mainly comprising TFE and has a melt operable property.

Examples of useful monomers are hexafluoropropylene (hereinafter referred to as "HFP"), perfluorovinyl ether, ethylene, propylene, etc., among which HFP is especially preferable. TFE is copolymerized with the other monomers in a ratio of 98–40 wt.% of TFE to 2–60 wt.% of the other monomers. The ratio is suitably variable within this range in accordance with the kind of the monomer used. The copolymer can be prepared by any of various conventional methods. Examples of preferably copolymers are:

(1) Copolymer of TFE and HFP in a ratio of 95:5 to 75:25 by weight (hereinafter referred to as "TFE-HFP" copolymer).
(2) Copolymer of TFE and perfluorovinyl ether in a ratio of 98:2 to 90:8 by weight.
(3) Copolymer of TFE and ethylene in a ratio of 70:30 to 90:10 by weight.
(4) Copolymer of TFE, ethylene and propylene in a ratio of (40–60):(25–50):(2–20) by weight.

Among these, TFE-HFP copolymer is easily available and therefore more preferable. However any of these copolymers is in itself chemically very inert like PTFE and will not adversely affect, or react with, the body tissue.

FIG. 1 shows a suture of this invention filled with TFE-HFP copolymer and obtained in Example 1 given later, and FIG. 2 shows a conventional suture impregnated with PTFE and obtained in Comparison Example 1 given later. The PTFE-impregnated suture of FIG. 2 has numerous fine fibrous whiskers on the surface, whereas the TFE-HEP-filled suture of FIG. 1 has none of such whiskers.

Figure 1:
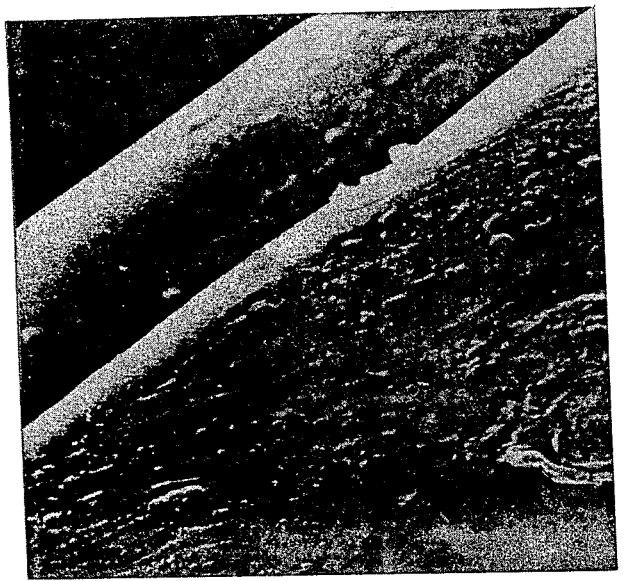
FIGS. 1 and 2 are photographs showing the surfaces of sutures as observed under a scanning electron microscope at a magnification of 5000X.

The TFE copolymer is incorporated into the multifilamentous material in an amount of about 1 to about 30% by weight as already mentioned, preferably about 5 to about 15% by weight, based on the weight of the material. With a lesser amount of the copolymer present, the resulting suture fails to have a sufficiently reduced coefficient of friction and improved slipping properties. Since the interstices of the multifilamentous material are then filled with the copolymer only to a small extent, the human body tissue will enter and attach to the suture, or bacteria will enter the suture to cause infection of the sutured tissues. When the copolymer is incorporated in an amount larger than the above range, the suture becomes stiff in its entirety and has impaired knotting characteristics, hence undesirable.

The multifilamentous suture to be used as the material of the suture of this invention can be any of those heretofore used. Typically the suture is made of silk, collagen or like natural material, or polyester, nylon, polypropylene or like synthetic material. Since the TFE copolymer incorporated into the suture material in the manufacturing process is baked at a high temperature as will be described below, it is preferable to select a material which has the highest possible resistance to heat.

The suture of this invention is prepared by immersing a multifilamentous surgical suture in a dispersion of particles of TFE copolymer of 100–500 mμ in average particle size to incorporate the copolymer into the suture and drying the suture to remove the medium of the dispersion. To ensure deposition and penetration of the copolymer, it is desirable that the immersion bath be provided with means such as suture guides or compressing rolls for passing the suture between the rolls. The concentration of the TFE copolymer dispersion can be about 5 to about 60%. To permit the suture to retain the multifilamentous surface structure to the greatest possible extent, the suture can be immersed in a dispersion of high concentration first, then in a dispersion of lower concentration or in the medium only of the dispersion, and thereafter withdrawn.

After the TFE copolymer has been incorporated into the suture by the above procedure, the portion of the copolymer which is present at least in the vicinity of the surface of the suture is baked, whereby the coefficient of friction of the suture can be reduced. Unless the copolymer is so baked, the resulting suture, when used, is likely to release particles of the copolymer from its surface since the adhesion of the copolymer to the suture is weaker. It is of course desirable to bake the copolymer at a temperature not lower than the melting point of the copolymer. However, if the suture is heated in its entirety at such a high temperature, the fibrous material is very likely to melt or decompose. Accordingly there is the need to employ some means by which chiefly the copolymer alone can be heated for a short period of time. We have found that a far infrared lamp is useful for this purpose. The far infrared lamp is a lamp for emitting far infrared rays which are infrared rays having wave lengths of about 1 cm to about 300 cm. According to this invention, the far infrared lamp is used for baking the suture. Although the copolymer need not always be melted by the baking, it is preferable to melt the copolymer to form a surface of improved smoothness. The conditions under which the far infrared lamp is used for baking are not particularly critical. Thus the suture may be illuminated by any of various far infrared lamps for a suitable period of time. The suture is illuminated generally for 5 seconds to 5 minutes, preferably for 20 seconds to 1 minute. However, the illumination time must be adjusted in accordance with the interior temperature of the oven in which the suture is treated, the quantity of the suture to be treated therein, the volume of the oven, etc. The baking treatment produces a gloss on the surface of the suture, so that the suture must be baked for at least such a period of time varys necessary for producing the surface gloss. Thus, only the portion of the TFE copolymer which portion is located mainly in the surface layer of the suture is baked by the lamp to form a tough coating, which reduces the coefficient of friction of the suture and the adhesion of the suture to the human body tissue. Preferably the suture is stretched when it is dried as stated above or when it is heated by the far infrared lamp to thereby reduce the interstices in the suture and to fill the suture with the copolymer to a greater extent. The process of treating the suture thus described is conducted continuously with the result that the process can be finished for more shortened period.

A multifilamentous polyester suture of U.S. Standard 4-0 (referred to as "the thread" hereinafter) which has a six polyester filament core of 30 denier and a braided cover made with a twelve carrier braider made of the same polyester filament is immersed in a 10% aqueous dispersion of copolymer of TFE and HFP (90:10 by weight) having a mean particle size of 190 mμ, then withdrawn and thereafter continuously dried at about 120° C. by being illuminated with an infrared lamp. The amount of the copolymer thus incorporated into the thread is 10% based on the weight of the thread. The dried thread is placed into a far infrared oven (the product of TOSHIBA DENZAI CO., LTD., Japan, "KRS-21028", 30×30×40 cm) having 8 far infrared lamps and a current of 5 to 10 A is passed through the lamps to maintain the interior temperature of the oven at 200° C., and about 30 seconds later, is stretched longitudinally by 20% within the oven, whereby a suture of this invention is obtained.

The suture having the TFE-HFP copolymer incorporated therein is tested for frictional resistance and knotting properties by the following methods.

Frictional resistance:

Measured with use of tension and compression tester (electron tube type, "Strograph" of Toyo Seiki Co., Ltd.) by contacting the sutures with themself crosswise at 90 degrees at a temperature of 20° C. and at a humidity of 45%.

Knotting characteristics:

Measured by the usual method of surgical knot. The knotted suture is stretched while increasing the number of the additional twist after turning the first overhand, and the number of the additional twist before the suture is unknotted is counted. The characteristics are expressed in terms of the resulting count plus one.

Table 1 shows the test results. Further, FIG. 1 is a scanning electron photomicrograph showing the suture. It is seen that the suture of this invention has none of fine fibrous whiskers.

COMPARISON EXAMPLE 1

Figure 2:

The same thread as used in Example 1 is treated in the same manner as above except that a 10% aqueous dispersion of PTFE is used in place of the aqueous dispersion of PFE-HFP copolymer to impregnate the thread with 10% by weight of PTFE. The thread is then dried at 120° C. with an infrared lamp, and illuminated by a far infrared lamp and stretched as the same way as in Example 1. The suture obtained is tested in the same manner as in Example 1. Table 1 shows the results. FIG. 2 is a scanning electron photomicrograph of the suture, which shows numerous fine fibrous whiskers formed on the suture.

EXAMPLE 2

The same thread as used in Example 1 having TFE-HFP copolymer incorporated therein and dried in the same manner as in Example 1 is placed into the far infrared oven set at a temperature of 220° C., and about 30 seconds later, is stretched longitudinally by 20% within the oven, whereupon the thread is withdrawn.

The suture thus obtained is tested in the same manner as in Example 1, with the results shown in FIG. 1.

EXAMPLE 3

The same thread as used in Example 1 is treated in the same manner as in Example 1 with the exception of using, in place of the PFT-HFP copolymer dispersion, a 10% aqueous dispersion of copolymer of TFE and perfluoropropylvinyl ether (97:3 by weight) having a means particle size of 210 mμ, and also setting the far infrared oven at a temperature of 250° C.

The suture obtained is tested in the same manner as in Example 1, with the results listed in Table 1.

TABLE 1

| | Thread | Example 1 | Example 2 | Example 3 | Comp. Ex. 1 |
|---|---|---|---|---|---|
| Frictional resistance (g) | 270 | 180 | 170 | 180 | 200 |
| Knotting characteristics (count) | 2 | 3 | 3 | 3 | 4 |
| Appearance of suture surface* | | No whiskers (FIG. 1) | No whiskers and smooth-surfaced | No whiskers | Many whiskers (FIG. 2) |

*As observed under electron microscope.

We claim:

1. A surgical suture characterized in that a multifilamentous suture has incorporated in its interstices a copolymer of tetrafluoroethylene and the other copolymerizable monomer in an amount of about 1% to about 30% by weight based on the weight of the multifilamentous suture, the copolymer being of 100–500 m$\mu$ in mean particle size, and that the portion of the copolymer present at least in the vicinity of the surface of the suture has been baked.

2. A suture as defined in claim 1 wherein said the other monomer is at least one of hexafluoropropylene, perfluorovinyl ether, ethylene and propylene.

3. A suture as defined in claim 1 wherein the copolymer is composed of tetrafluoroethylene and hexafluoropropylene in a ratio of 95:5 to 80:20.

* * * * *